US006555817B1

(12) United States Patent
Rohde et al.

(10) Patent No.: US 6,555,817 B1
(45) Date of Patent: Apr. 29, 2003

(54) METHOD AND APPARATUS FOR CORRECTING MAGNETIC FIELD DISTORTIONS IN ELECTRON BACKSCATTER DIFFRACTION PATTERNS OBTAINED IN AN ELECTRON MICROSCOPE

(75) Inventors: David Rohde, Madison, WI (US); Patrick P. Camus, Middleton, WI (US)

(73) Assignee: Thermo Noran Inc., Middleton, WI (US)

( * ) Notice: Subject to any disclaimer, the term of this patent is extended or adjusted under 35 U.S.C. 154(b) by 0 days.

(21) Appl. No.: 09/572,198

(22) Filed: May 17, 2000

(51) Int. Cl.[7] .......................... G21K 7/00; G21K 37/08; A61N 5/00; H01J 37/26
(52) U.S. Cl. ............... 250/311; 250/492.3; 250/492.22; 250/550
(58) Field of Search ................................. 250/311, 310, 250/306, 307; 73/763, 774, 78; 358/521; 382/141, 151, 216, 296

(56) References Cited

U.S. PATENT DOCUMENTS

| 4,574,311 | A | * | 3/1986 | Resnikoff et al. ........... 348/315 |
| 4,990,779 | A | | 2/1991 | Yoshitomi et al. |
| 5,466,934 | A | | 11/1995 | Adams et al. |
| 5,557,104 | A | | 9/1996 | Field et al. |
| 5,734,384 | A | * | 3/1998 | Yanof et al. ................. 345/419 |
| 5,809,213 | A | * | 9/1998 | Bhattacharjya ............. 358/1.6 |
| 6,067,164 | A | * | 5/2000 | Onoguchi et al. .......... 250/307 |
| 6,067,379 | A | * | 5/2000 | Silver ........................ 382/151 |
| 6,075,881 | A | * | 6/2000 | Foster et al. ................ 382/141 |
| 6,091,519 | A | * | 7/2000 | Ito .............................. 358/521 |
| 6,212,420 | B1 | * | 4/2001 | Wang et al. ................. 382/128 |
| 6,215,915 | B1 | * | 4/2001 | Reyzin ....................... 345/648 |
| 6,282,328 | B1 | * | 8/2001 | Desai ......................... 382/205 |
| 6,326,619 | B1 | * | 12/2001 | Michael et al. ............. 250/307 |

FOREIGN PATENT DOCUMENTS

JP 59182348 A * 10/1984 .......... G01N/23/20

OTHER PUBLICATIONS

William H. Press, et al., Numerical Recipes in C, pp. 94–98.

* cited by examiner

*Primary Examiner*—Bruce Anderson
*Assistant Examiner*—Bernard Souw
(74) *Attorney, Agent, or Firm*—Foley & Lardner

(57) ABSTRACT

A system and method for correcting automatically the distortions in electron background diffration (EBSD) patterns which result from magnetic fields produced by some scanning electron microscopes (SEMs) used for collecting such patterns from polycrystalline sample materials. The method may be implemented as a software program running on a computer which is part of a conventional system for obtaining and analyzing EBSD patterns to obtain crystallographic information about the sample material. The method includes a calibration procedure and a correction procedure. In the calibration procedure, a distorted EBSD pattern obtained from a calibration sample is displayed on an operator display and user interface. Using an input device, an operator defines segment endpoints along a Kikuchi band in the distorted EBSD pattern image. From the user defined segment endpoints, correction parameters are calculated based on a mathematical curve (e.g., cubic spline) fitting the endpoints. The correction parameters may also be corrected automatically, without user intervention. The correction parameters are saved and may be used to correct magnetic field distortions in all subsequent EBSD patterns obtained using the SEM geometry for which the calibration procedure is run. In the correction procedure, the correction parameters are employed to shift lines of pixels in the distorted EBSD pattern image by an amount defined by the correction parameters to correct the distortion in the EBSD pattern image. Thus corrected EBSD pattern images may be displayed to a operator of the system and saved for subsequent EBSD pattern analysis using conventional EBSD pattern analysis techniques.

31 Claims, 4 Drawing Sheets

METHOD AND APPARATUS FOR CORRECTING MAGNETIC FIELD DISTORTIONS IN ELECTRON BACKSCATTER DIFFRACTION PATTERNS OBTAINED IN AN ELECTRON MICROSCOPE

FIELD OF THE INVENTION

The present invention pertains generally to systems and methods for analyzing diffraction patterns obtained from an electron microscope and, more particularly, to a method and apparatus for correcting distortions in diffraction patterns obtained from crystalline specimens using an electron microscope.

BACKGROUND OF THE INVENTION

Scanning electron microscopes (SEMs) are used to investigate and characterize features within sample materials of interest. For example, an SEM may be used to obtain crystallographic information, e.g., the size and shape of constituent crystals or grains, the orientation of crystal lattices, and the spatial location of the crystals within a polycrystalline material. Based on such crystallographic information, the properties and characteristics of the material may be determined. Such information is useful for understanding why certain crystalline materials behave as they do, to predict how other materials will behave, and to alter or to otherwise control material forming and processing techniques to improve specific material properties.

A typical procedure for determining the crystallographic characteristics of a polycrystalline sample specimen involves bombarding selected points of the specimen with a beam of electrons produced by an SEM. The electrons interact with a small volume of the material sample at the selected points, and diffracting crystals cause electron backscatter diffraction (EBSD) patterns to form on a detector, e.g., a phosphorous screen, placed near the specimen in the SEM. The EBSD patterns may be imaged through a video camera, and digitized for further processing. Good quality EBSD patterns include a number of intersecting, relatively high intensity bands that are usually referred to as Kikuchi bands, which result from electrons being diffracted from various planes in the crystal lattice at the point of bombardment. An abundance of microstructure information may be obtained by analyzing the various parameters of the Kikuchi bands. Computer-implemented image processing techniques have been developed to analyze Kikuchi bands from the EBSD patterns taken at numerous points on a material sample, and to generate displays of the crystalline specimen that convey a wealth of microstructure information.

A problem arises when EBSD patterns are obtained using certain SEMs (immersion-lens SEMs) which employ a final (objective) electron lens, for focusing and directing the electron beam, which produces large magnetic fields near the sample being analyzed. Although these magnetic fields are required for superior image resolution, they are detrimental to quality EBSD pattern formation in that the fields distort the near-linear trajectory of the electrons emerging from the sample, thereby distorting the EBSD pattern which is detected by the detector. EBSD patterns are distorted by these magnetic fields such that features that should appear straight, if detected using a conventional SEM which does not produce such fields, are curved in the EBSD pattern images obtained using an SEM which does produce such fields. Accurate analysis of such distorted EBSD pattern images is impossible. Thus, SEMs which produce magnetic fields which distort EBSD patterns cannot be used for crystallographic structure analysis unless the distortion in the EBSD pattern can be avoided or corrected.

In general, users tend to avoid using SEMs which produce magnetic fields which distort EBSD patterns for EBSD pattern analysis. This is unfortunate, since such SEMs otherwise provide superior image resolution. If EBSD pattern analysis systems are employed with such SEMs, abnormal geometric mounting of the SEM electron beam generator and EBSD pattern collection system may be possible to avoid magnetic field distortion of the EBSD pattern image. However, such a modification will be at the expense of SEM imaging quality and EBSD pattern collection performance. Since the magnetic field strengths and distributions employed in SEMs are highly guarded secrets of the various SEM manufacturers, and are not generally available to the public or to developers of EBSD pattern analysis systems, correction of distorted EBSD pattern images cannot come from physical modeling of the distorting magnetic fields.

What is desired, therefore, is a system and method for correcting automatically the distortion in EBSD pattern images obtained using SEMs which generate pattern distorting magnetic fields, which is based only upon available empirical information, and which produces corrected EBSD pattern images which may be analyzed using conventional EBSD pattern analysis techniques.

SUMMARY OF THE INVENTION

The present invention provides a system and method for correcting automatically the distortions in EBSD patterns which result from the magnetic fields generated in some SEMs used for collecting such patterns. A method for correcting magnetic field distortions in an EBSD pattern in accordance with the present invention may be implemented as a software program running on a computer which is part of a conventional system for obtaining and analyzing EBSD patterns. The first time that the correction method is run for a particular SEM geometry, a calibration procedure is run to obtain pattern distortion correction parameters based on a single or multiple mathematical curves extracted from a calibration image. These correction parameters may be employed each time an EBSD pattern image is obtained using this SEM geometry to correct automatically any magnetic field distortion in the EBSD pattern. Traditional EBSD pattern analysis methods may be used to analyze such corrected EBSD patterns to obtain crystallographic structure information for a sample being analyzed. The present invention provides for correcting automatically a distorted EBSD pattern based solely on empirical information. Thus, the present invention may be employed in combination with any SEM used for EBSD pattern collection without the need for any data on the particular magnetic field strengths and distributions employed in the SEM. Furthermore, the present invention may be used to obtain distortion-free EBSD patterns for analysis without abnormal geometric mounting of the SEM electron beam generator, sample, and pattern collection system, which might adversely affect SEM imaging and EBSD pattern collection performance.

In accordance with the present invention, an EBSD pattern may be obtained in a conventional manner using a conventional EBSD pattern collection and analysis system. For example, a sample, e.g., of a polycrystalline material, may be mounted in an SEM and bombarded by an electron beam. Backscattered electrons from the sample are detected, in a conventional manner, by a detection and imaging system including a detector, e.g., a phosphorous screen, a camera, for recording the image produced by the detector, and a digitizer, for digitizing the video image and providing it to a computer system for EBSD pattern analysis. Any distortion in the EBSD pattern image which results from the magnetic fields produced by the final (objective) electron lens in the SEM must be corrected before analysis of the EBSD pattern is performed. In accordance with the present invention, the distorted EBSD pattern may be corrected by a correction method implemented as a software program, which may be run on the same computer which is employed for EBSD pattern analysis.

In accordance with the present invention, a distorted EBSD pattern is corrected using correction parameters based on a single or multiple mathematical curves which are used to shift the intensity values in the distorted EBSD pattern image, pixel line by pixel line, to remove any magnetic field distortion therefrom to provide as nearly a distortion-free image as possible. The correction patterns are obtained by performing a calibration procedure. Once the calibration procedure has been performed, the correction parameters obtained may be used to correct the distortion in all subsequent EBSD pattern images obtained using the particular SEM geometry for which the calibration procedure was run.

In the calibration procedure, a distorted EBSD pattern is obtained in a conventional manner as described above from a known crystalline material calibration sample. For example, a silicon calibration sample <100> with the low index direction mounted vertically in the SEM may be used. The EBSD pattern thus obtained, which is distorted by magnetic fields in the SEM, is displayed on an operator display. The operator display, in combination with a user input device, such as a mouse, forms a user interface for the calibration procedure. Using the user input device, e.g., the mouse, an operator defines segment endpoints along a low index Kikuchi band (represented by the low index direction) in the distorted EBSD pattern image displayed. The result is a segmented curved line following the curved Kikuchi band in the distorted EBSD pattern. In a non-distorted EBSD pattern, the Kikuchi band would follow a straight line. From the user-defined segment endpoints, the calibration procedure calculates a single or a series of mathematical curves to fit. For example, a cubic spline or polynomial curve may be calculated. The mathematical curve or curves define the amounts by which points along the user-defined curved line must be shifted in order to form a straight line. These correction parameters are saved into a pattern correction parameter data file. Alternatively, the correction parameters may be calculated in a more automated fashion.

The correction parameters obtained in the calibration procedure are employed in a correction procedure to correct the magnetic field distortions in EBSD patterns collected using the SEM geometry for which the calibration procedure was performed. Having obtained an EBSD pattern in a conventional manner using the distorting SEM system, the stored correction parameters are retrieved and are employed to shift lines of pixels in the distorted EBSD image by an amount defined by the correction parameters to correct the distortion in the EBSD pattern image. For example, the intensities of each line in the distorted EBSD pattern image may be shifted, row-by-row, by the amount determined by the mathematical curve calculation for each vertical position in the image. Any "unfilled" region of the EBSD pattern image which is created by the shifting operation may be filled with an intensity equal to the average intensity of the whole image (thereby creating a curved "wedge" feature along one side of the image). The thus corrected EBSD pattern image may be displayed to an operator of the system, and saved for subsequent EBSD pattern analysis using conventional EBSD pattern analysis techniques.

Further objects, features, and advantages of the present invention will be apparent from the following detailed description taken in conjunction with the accompanying drawings.

DETAILED DESCRIPTION OF THE INVENTION

Figure 1:
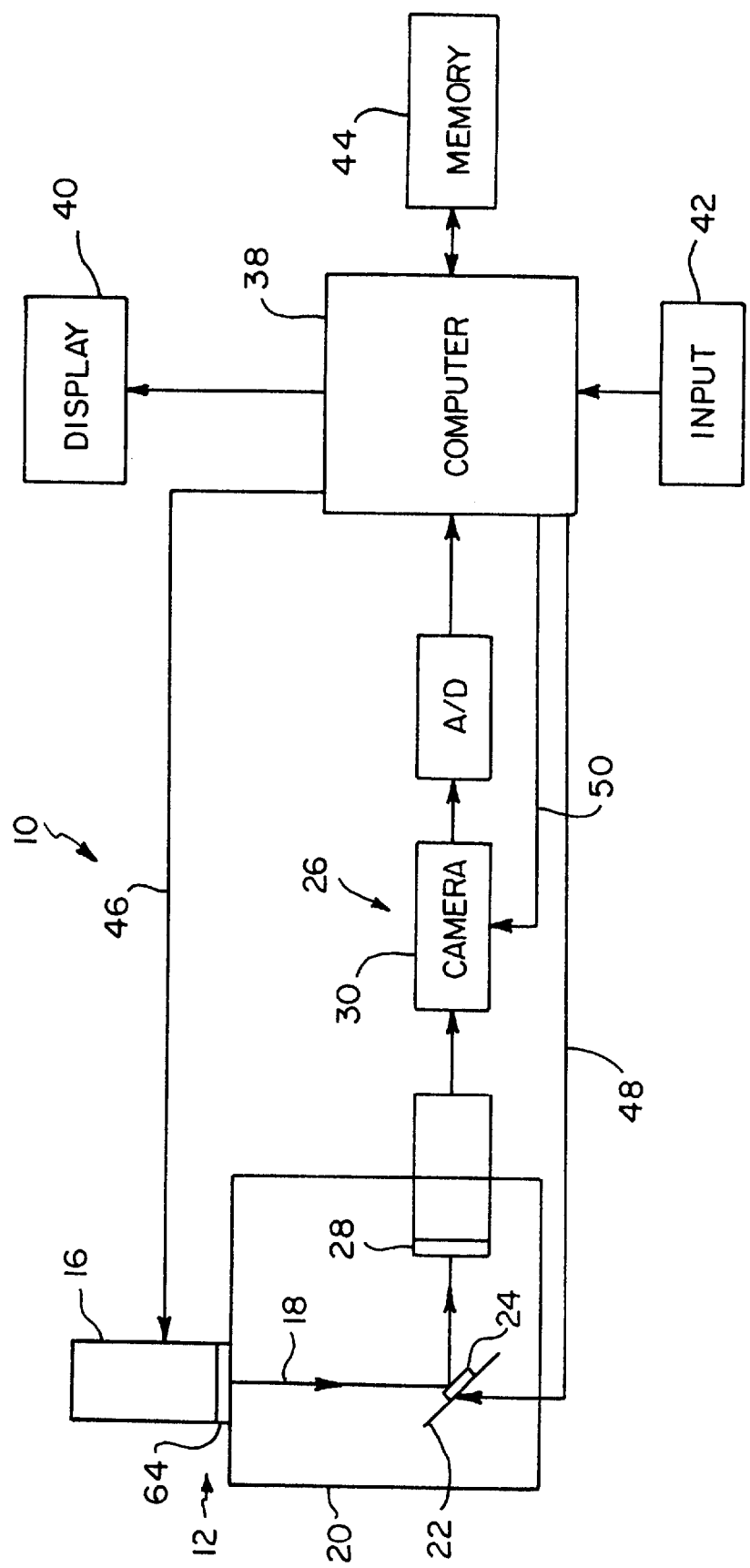
FIG. 1 is a schematic block diagram of an electron microscope and apparatus for obtaining EBSD patterns from a sample, for correcting magnetic field distortions in the EBSD patterns in accordance with the present invention, and for analyzing the corrected EBSD patterns to obtain crystallographic information for the sample.

An exemplary system 10 for obtaining EBSD patterns from polycrystalline samples, for correcting distortions in the EBSD patterns resulting from magnetic fields produced by a scanning electron microscope (SEM), and for analyzing the corrected EBSD patterns to obtain crystallographic information for the samples, is illustrated in FIG. 1, and will be described in detail with reference thereto. It should be noted that any of various conventional hardware configurations for collecting EBSD patterns using an SEM may be employed to implement the system 10, and conventional methods may be employed for obtaining EBSD pattern images using the system 10 and for analyzing EBSD patterns which have been corrected to remove magnetic field distortions therefrom using a method in accordance with the present invention.

The system 10 includes a conventional SEM 12. Those skilled in the art will recognize, however, that the system 10 may utilize other types of microscopes for investigating and characterizing the features within a sample of interest using electron or other energy beams, depending upon the specific application. For example, a transmission electron microscope may be used. The SEM includes an electron beam generator 16, which discharges a focused electron beam 18 into a vacuum chamber 20. A holding stage 22 is mounted in the vacuum chamber 20 such that a material specimen 24 mounted thereon is bombarded or illuminated by the electron beam 18.

An image collection system 26 is utilized to collect images of backscattered electrons diffracted from specimen 24. The image collection system 26 includes a detector 28, e.g., a screen that is coated with a scintillating material, such as phosphorous, for detecting the electrons backscattered from the sample 24. The detector 28 is coupled to a video camera 30 in a conventional manner. The detector 28 luminesces in accordance with the pattern of the diffracted electrons falling thereon. The resulting electron backscatter diffraction (EBSD) patterns are captured by the video camera 30, where they are converted into electronic signals, which are converted into digital data in an image digitizer 36.

The digitized EBSD pattern image is provided from the digitizer 36 to a computer system 38 whereby the EBSD pattern is displayed and wherein the EBSD pattern is corrected for magnetic field distortion in accordance with the present invention and analyzed to obtain crystallographic information for the sample 24 in a conventional manner. The computer system 38 may be implemented as a conventional computer system. The computer 38 includes conventional computer components and peripheral devices, including computer output devices, such as a system or operator display 40, e.g., a computer monitor, and input devices 42, such as a keyboard, mouse, trackball, etc. The computer 38 also includes computer memory 44, such as disk storage memory, which stores programming instructions which define various processes carried out by the computer system 38, including programming instructions implementing a method for correcting magnetic field distortions in EBSD patterns in accordance with the present invention, and correction parameters used in such a method. Conventional computer programs for analyzing EBSD patterns to obtain crystallographic information may also be stored in memory 44, along with saved EBSD pattern images and analysis results. The computer 38 also controls the SEM beam generator 16, movement of the sample holding stage 22, and the image collection system 26, in a conventional manner, e.g., via control lines 46, 48, and 50, respectively. As is known in the art, the system 10 may be controlled to collect EBSD patterns from a series of points on a specimen 24 to provide an analysis of the entire structure of the specimen 24.

Figure 2:
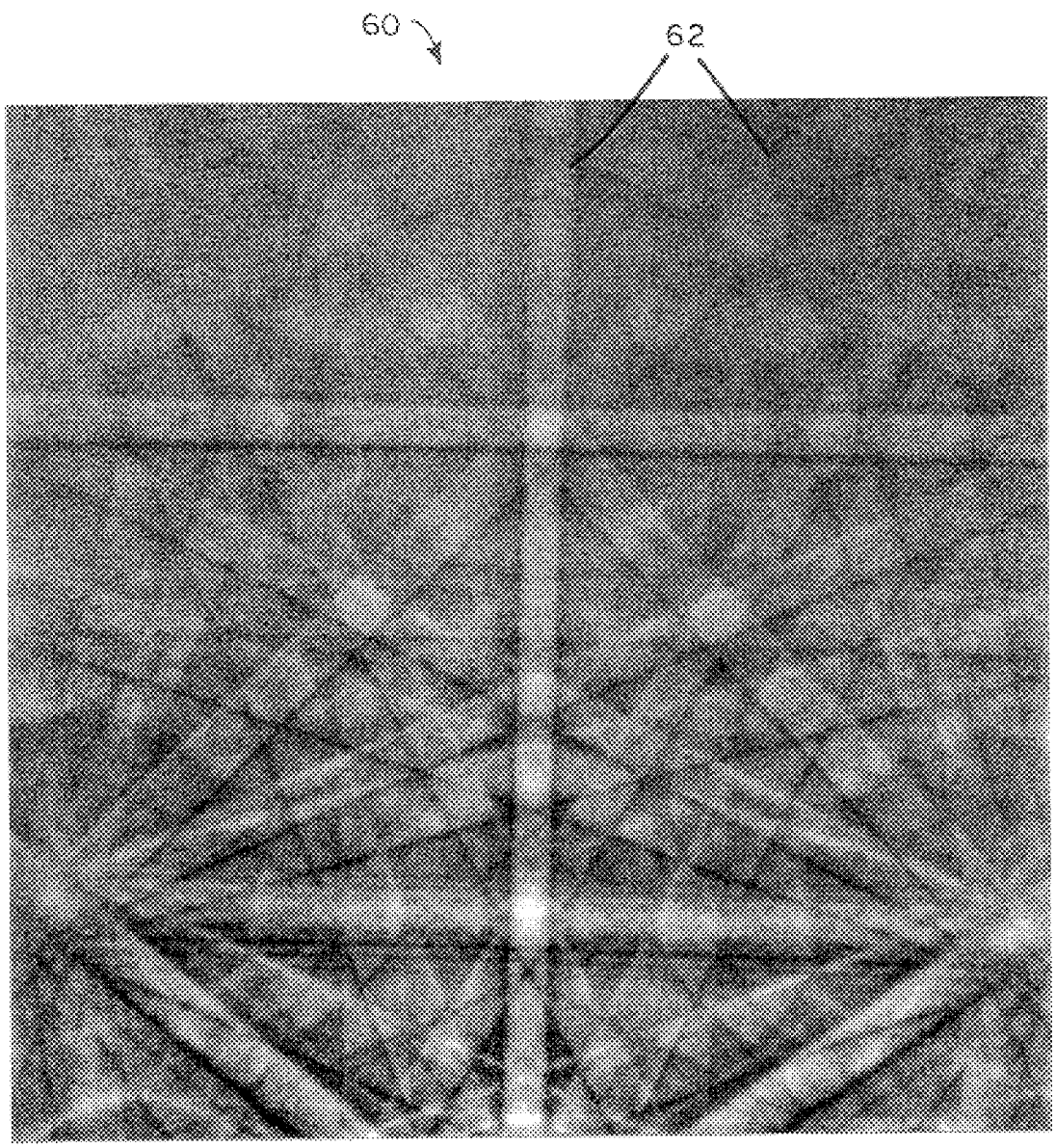
FIG. 2 is an exemplary display of a conventional undistorted EBSD pattern image.

An exemplary (undistorted) EBSD pattern 60, which may be obtained by a conventional EBSD pattern collection system 10, and displayed on the operator display 40, is shown in FIG. 2. The EBSD pattern 60 includes a plurality of bands 62 (typically referred to as Kikuchi bands) formed by the diffraction of the electron beam 18 by the crystalline structure of the sample 24. The Kikuchi bands 62 intersect each other and are generally bordered by thin lines of lower intensity. Conventional analysis programs and techniques are available for analyzing the Kikuchi bands 62 to obtain crystallographic information for the sample 24 from the EBSD pattern. Note how the Kikuchi bands 62 in the EBSD pattern 60 run straight.

Certain SEMs (immersion-lens SEMs) employ a final (objective) electron lens 64 (FIG. 1) for directing and focusing the electron beam 18. Such a lens 64 produces magnetic fields which may extend into the vacuum chamber 20 near the sample 24. Although these magnetic fields are required for superior image resolution, they also distort the near-linear trajectory of the electrons diffracted from the sample 24 into curved paths, thereby distorting the resulting EBSD pattern. An exemplary distorted EBSD pattern which may be obtained using such an SEM system is illustrated at 66 in the left side of FIG. 3. (This EBSD pattern 66 was obtained from the same sample as was used to obtain the EBSD pattern 60 as shown in FIG. 2.) Note how the Kikuchi band 68, which should run straight, is bent in the distorted EBSD pattern image 66 (compare EBSD pattern 66 of FIG. 3 with EBSD pattern 60 of FIG. 2). Accurate analysis of such a distorted EBSD pattern using conventional EBSD pattern analysis systems is impossible. The present invention, however, provides a system and method for correcting automatically the magnetic field distortions in EBSD patterns, thereby allowing conventional analysis of EBSD patterns to obtain crystallographic information therefrom. Since the magnetic field strengths and distributions employed in SEMs are not generally available, the present invention provides EBSD pattern correction based only upon available empirical information.

Figure 3:
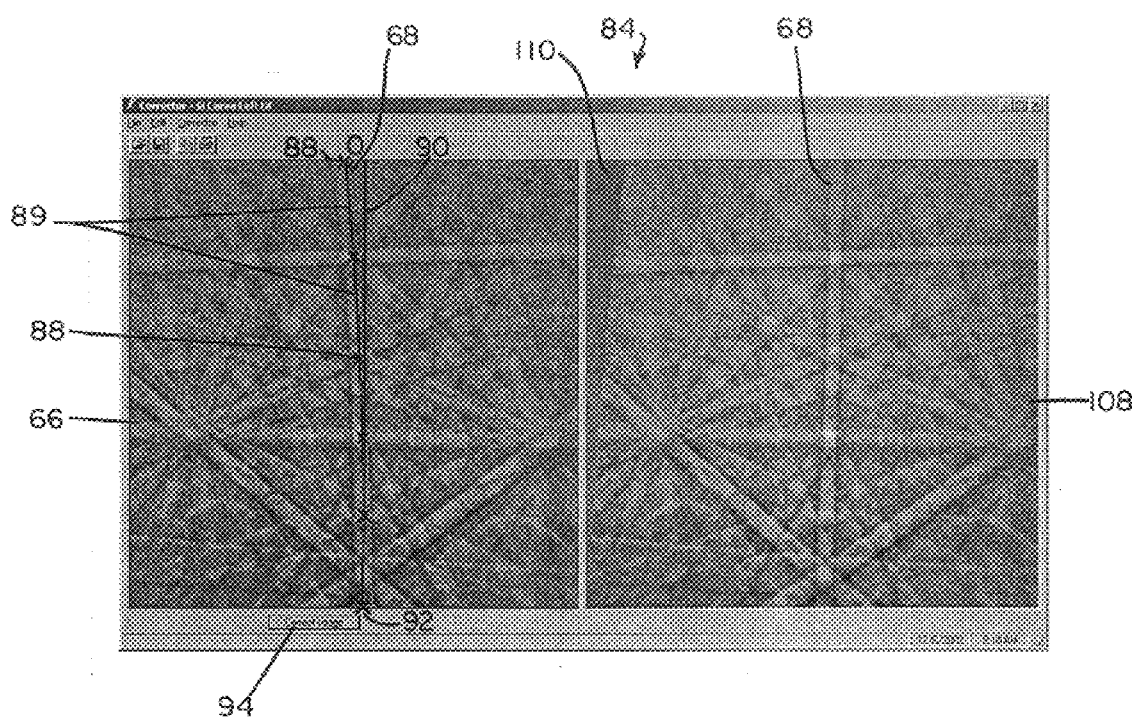
FIG. 3 is an exemplary display of a distorted EBSD pattern image as used in a calibration procedure in accordance with the present invention, and a corresponding corrected EBSD pattern obtained by applying an EBSD pattern correction procedure in accordance with the present invention to the distorted EBSD pattern image.
Figure 4:
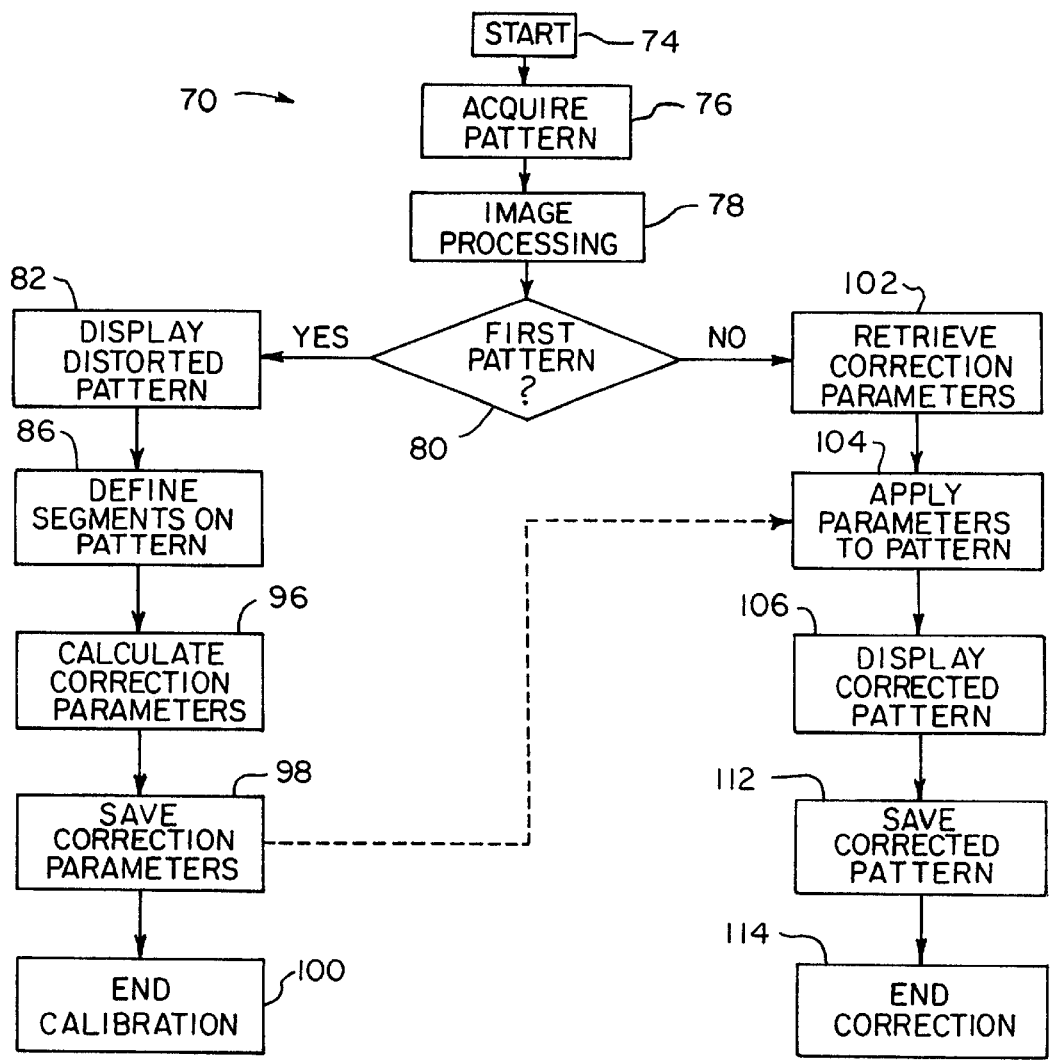
FIG. 4 is a flowchart diagram of an exemplary method for correcting magnetic field distortions in EBSD patterns in accordance with the present invention, including calibration and correction procedures.

An exemplary method 70 in accordance with the present invention for correcting an EBSD pattern which has been distorted by the magnetic field produced by an SEM will now be described in detail with reference to FIG. 3 and to the flowchart diagram of FIG. 4. The method 70 of the present invention to be described below may be implemented in a conventional computer 38 in a conventional manner, using conventional computer programming techniques in, for example, a Windows-based operating system or any other conventional operating system and using any conventional programming language.

The method 70 for correcting the magnetic field distortions in EBSD patterns in accordance with the present invention may be started 74 each time an EBSD pattern is collected, e.g., using conventional methods and the system 10 as described above, and may be applied to each EBSD pattern collected to correct any distortion created by the magnetic field produced by the SEM 16. As described above, an EBSD pattern is acquired 76, digitized, and provided to the system computer 38 in a conventional manner. Conventional image processing 78 may be applied to the EBSD pattern image thus obtained in the normal manner. For instance, such conventional processing may include image brightness and contrast adjustment, background removal, etc.

A determination 80 then is made whether this is the first EBSD pattern obtained using this particular SEM geometry. If this is the first EBSD pattern obtained using the SEM geometry, the distortion correction method of the present invention runs a calibration procedure, whereby parameters used for correcting the magnetic field distortion in the EBSD pattern are obtained. As will be discussed in more detail below, these parameters may be used for correcting the magnetic field distortion in all subsequent EBSD patterns obtained using the SEM geometry for which the calibration procedure was run.

In the calibration procedure, the first distorted EBSD pattern image obtained using a particular SEM geometry is displayed 82 to an operator on the operator display 40. The calibration procedure is preferably performed using an EBSD pattern obtained from a polycrystalline sample having a known crystal structure. For example, a silicon <100> calibration sample wafer may be mounted in the SEM 12 with the low-index direction mounted vertically. The resulting EBSD pattern includes a Kikuchi band 68 which runs vertically across the pattern but which is curved due to magnetic field distortion. Another type of calibration sample material may also be used. The distorted EBSD pattern thus obtained is displayed on the operator display 40 to provide an operator/user interface which allows an operator of the computer 38 to interact with the displayed EBSD pattern using an input device 42, such as a mouse, trackball, etc. An exemplary user interface 84 is illustrated in FIG. 3. Such a user interface may be generated using conventional programming techniques. It should be understood that other user interface designs and layouts may also be employed.

Using the user input device 42, e.g., a mouse, the operator defines 86 the endpoints 88 of line segments 89 along the length of a feature in the distorted EBSD pattern which is curved (distorted) but should be straight. In the example shown in FIG. 3, six segment endpoints 88 are defined in this manner along curved Kikuchi band 68 by the operator. It should be understood, however, that more or fewer endpoints 88 may be defined and used in this manner, and the number of segment endpoints to be used may be made user selectable. Having defined the segment endpoints 88, an operator may select the Correct Image button 94 on the user interface 84 to initiate the next step in the calibration procedure.

From the user-defined line segment endpoints 88, a single or series of mathematical curves fitting the points, and, therefore, the distorted linear feature 68, is calculated in a conventional manner. For example, a cubic spline or other polynomial which defines a curved line or lines running through each of the endpoints 88 defined by the operator using the user interface 84 may be calculated automatically in a conventional manner. The mathematical curve thus calculated defines the curvature of, e.g., the Kikuchi band 68 in the distorted EBSD pattern 66. As discussed above, in an undistorted EBSD pattern, the Kikuchi band 68 would run straight. Therefore, in accordance with the present invention, the mathematical curve or curves define correction parameters which define the distance of points along the Kikuchi band 68 from a straight line 90 which represents the direction that the Kikuchi band 68 should run in an undistorted pattern.

For example, the correction parameters may be calculated based on a cubic spline calculated relative to a straight line 90, which may be user defined and selected. For example, the straight line 90 may preferably be defined by an operator using the input device 42 to extend from a segment endpoint 92 located at one end of the Kikuchi band 68 vertically across the displayed EBSD pattern. If an EBSD pattern image from a known calibration sample is used, it may not be necessary for the user to define a straight line 90 on the operator display 84. In such a case, the undistorted Kikuchi band may be assumed to run vertically across the EBSD pattern beginning at the segment endpoint 92 defined at the end of the Kikuchi band. The cubic spline may be calculated in a conventional manner using the X and Y data position segment endpoints 88 defined by the user along the Kikuchi band 68 to calculate the spline. (From six defined segment endpoints, a six-point cubic spline fit may be calculated, but, as discussed above, more or fewer segment endpoints could be used.) The segment relative X and Y endpoints are input into a routine and four cubic spline coefficients are calculated for each endpoint. The cubic spline effectively defines the amount of bend in the distorted Kikuchi band 68 along the length of the band. In other words, the cubic spline defines the distance of points along the Kikuchi band 68 in the distorted EBSD pattern from a corresponding point, in the same vertical position, along the straight line 90. The cubic spline thus defines correction parameters which define the amount by which the picture elements (pixels) in each vertical row in the distorted EBSD pattern 66 must be shifted, in a horizontal direction, to correct for the magnetic field distortion in the EBSD pattern 66. Because the correction is relative in the horizontal direction, the base position is subtracted from each data point. This results in no shift for the bottom point of the bottom segment for, e.g., the example shown in FIG. 3.

The correction parameters thus calculated by the calibration procedure are saved at step 98. The parameters that may be saved are, for example, the number of cubic spline segments and the four cubic spline parameters for each segment endpoint and the vertical position of each endpoint.

The calibration procedure is now complete 100. The correction parameters determined by the calibration procedure may now be applied to the EBSD pattern 66 used during the calibration procedure to correct for magnetic field distortion of the EBSD pattern 66 in a manner to be described in more detail below. The saved correction parameters are also used to correct for magnetic field distortion in subsequent EBSD patterns obtained using the same SEM geometry. Thus, it is not necessary to perform the calibration procedure each time an EBSD pattern is obtained.

The correction parameters which are established using the calibration procedure may be retrieved from memory each time an EBSD pattern is acquired as the first step 102 in an EBSD pattern correction procedure. The correction parameters are applied to the distorted EBSD pattern at step 104 to adjust the EBSD pattern image to correct for magnetic field distortions thereof. This is performed, for example, row-by-row by shifting the intensities of each line of pixels in the distorted EBSD pattern image by the amount determined by the mathematical curve (e.g., cubic spline) calculation for that vertical position in the EBSD pattern. For example, for the exemplary distorted EBSD pattern image 66 illustrated in FIG. 3, the intensities of the pixels in the top row of pixels in the image are shifted to the left by distance D. The next row of pixels in the image would be shifted by a slightly smaller amount, and so on down the entire vertical length of the EBSD pattern image 66.

The resulting corrected EBSD pattern image 108 may then be displayed 106 to an operator on the operator display 40. For example, EBSD pattern 108 displayed in the right side of operator display 84 of FIG. 3 shows the distorted EBSD pattern 66 after being corrected by application of the pattern correction method of the present invention. Note that in the corrected EBSD pattern 108 the low index Kikuchi band 68 runs straight across the EBSD pattern 108.

Shifting of the rows of pixels in the distorted EBSD pattern in accordance with the present invention will create a portion of the image space which is "unfilled" by the obtained corrected EBSD pattern image. The result will typically be a curved "wedge" feature 110 along one side of the corrected EBSD pattern image 108. This "unfilled" area may be filled with pixels of a selected intensity, such as pixels of an intensity equal to the average intensity of the whole corrected EBSD pattern image 108.

EBSD pattern images corrected in accordance with the present invention may be saved 112 before the correction procedure ends 114. Such corrected EBSD pattern images may be analyzed using conventional EBSD pattern analysis systems and software to determine crystallographic parameters of a sample from the corrected EBSD pattern images. For analysis purposes, an EBSD pattern image corrected in accordance with the present invention is indistinguishable from an undistorted EBSD pattern image which did not require correction in the first place. It should be noted that, once correction parameters are established using the correction procedure, the process of obtaining, correcting, displaying, and analyzing EBSD patterns may proceed automatically without further user intervention in the correction procedure.

It should be understood that the present invention is not limited to the particular exemplary applications and embodiments illustrated and described herein, but embraces all such modified forms thereof as come with in the scope of the following claims. In particular, the present invention is not limited to the particular steps or order of steps for the calibration and correction procedures as illustrated in FIG. 4 and described herein. Furthermore, although a calibration procedure requiring an operator manually to define line segment end points along a Kikuchi band in a distorted EBSD pattern is described herein, an entirely automated calibration procedure, which uses, e.g., a pattern matching technique, to automatically determine the required correction parameters from a distorted EBSD pattern image, without operator intervention, may also be employed.

What is claimed is:

1. A method for correcting distortions in an electron backscatter diffraction pattern image including lines of picture elements, comprising the steps of:

extracting values from a calibration image, the values corresponding to corrections in patterns that are distorted by magnetic fields when using electron backscatter diffraction (EBSD) in a scanning electron microscope (SEM); and shifting picture elements in an electron backscatter diffraction (EBSD) image by the extracted values to remove distortion from the EBSD image to create a corrected EBSD image.

2. The method of claim 1 wherein the EBSD image includes a curved band and wherein shifting picture elements in an EBSD image includes shifting picture elements in the EBSD image by the extracted values to straighten the curved band.

3. The method of claim 1 wherein shifting picture elements in an EBSD image produces an unfilled portion of the corrected EBSD image, and further comprising filling the unfilled portion of the corrected EBSD image with picture elements having a selected intensity.

4. The method of claim 3 wherein filling the unfilled portion of the corrected EBSD image includes filling the unfilled portion of the corrected EBSD image with picture elements having an intensity approximately equal to an average intensity of the picture elements in the EBSD image.

5. The method of claim 1 further comprising displaying the corrected EBSD image.

6. The method of claim 1 further comprising saving the corrected EBSD image.

7. A method for correcting distortions in an electron backscatter diffraction pattern image, comprising the steps of:

(a) calculating correction parameters for electron backscatter diffraction (EBSD) in a scanning electron microscope (SEM), the correction parameters defining an amount by which points along a curved band in a first distorted EBSD image are shifted to straighten the curved band;

(b) storing the correction parameters for use in correcting magnetic field distortions in EBSD patterns using a substantially similar SEM geometry; and (c) shifting picture elements in a second distorted EBSD image by selected amounts determined by the correction parameters to remove the distortion from the distorted EBSD image and create a corrected EBSD image.

8. The method of claim 7 wherein calculating the correction parameters comprises calculating a mathematical curve fitting the curved band.

9. The method of claim 8 wherein calculating a mathematical curve fitting the curved band comprises calculating a cubic spline fitting the curved band.

10. The method of claim 8 wherein calculating a mathematical curve fitting the curved band comprises:

(a) defining a plurality of segment endpoints following the curved band in the first distorted EBSD image; and (b) calculating the mathematical curve fitting the segment endpoints.

11. The method of claim 10 wherein defining a plurality of segment endpoints comprises:

(a) displaying the corrected EBSD image on an operator display; and (b) defining the plurality of segment endpoints following the curved band in the corrected EBSD image using an operator input device.

12. The method of claim 10 wherein calculating the mathematical curve comprises calculating four cubic spline coefficients for each segment endpoint.

13. The method of claim 7 further comprising shifting picture elements in a plurality of EBSD images for a particular SEM by amounts determined by the stored correction parameters.

14. The method of claim 7 wherein shifting picture elements in the second distorted EBSD image produces an unfilled portion of the corrected EBSD image, and further comprising filling the unfilled portion of the corrected EBSD image with picture elements having a selected intensity.

15. The method of claim 14 wherein filling the unfilled portion of the corrected EBSD image includes filling the unfilled portion of the corrected EBSD image with picture elements having an intensity approximately equal to an average intensity of the picture elements in the corrected EBSD image.

16. The method of claim 7 further comprising displaying the corrected EBSD image.

17. The method of claim 7 further comprising saving the corrected EBSD image.

18. A system for obtaining electron backscatter diffraction patterns from a sample and correcting distortions therein, comprising:

(a) an electron microscope configured to direct a beam of electrons onto a sample to be backscattered therefrom;

(b) an image collection system that provides an electron backscatter diffraction (EBSD) pattern image including lines of picture elements from the electrons backscattered from the sample;

(c) means for acquiring correction parameters defining selected amounts to correct a distortion in a calibration EBSD image; and (d) means for shifting picture elements in the EBSD pattern image by selected amounts to remove the distortion from the image to create a corrected EBSD pattern image.

19. The system of claim 18 wherein the electron microscope is a scanning electron microscope.

20. The system of claim 18 wherein the image collection system includes an image digitizer for providing a digitized electron backscatter diffraction pattern image including lines of picture elements and wherein the means for shifting picture elements in the EBSD pattern image includes a computer programmed to receive the digitized electron backscatter diffraction pattern image from the image collection system and to shift picture elements in the EBSD pattern image by selected amounts to remove the distortion from the image to create a corrected EBSD pattern image.

21. The system of claim 18 wherein the EBSD pattern image includes a curved band and wherein the means for shifting picture elements in the EBSD pattern image includes means for shifting picture elements in the electron backscatter diffraction pattern image by selected amounts to straighten the curved band.

22. The system of claim 21 wherein the means for calculating the correction parameters includes means for calculating a mathematical curve fitting the curved band.

23. The system of claim 22 wherein the means for calculating the mathematical curve includes means for calcuating a cubic spline fitting the curved band.

24. The system of claim 22 wherein the means for calculating the mathematical curve includes:
   (a) means for defining a plurality of segment endpoints following the curved band in the electron backscatter diffraction pattern image; and
   (b) means for calculating a mathematical curve fitting the endpoints.

25. The system of claim 24 wherein the means for defining a plurality of segment endpoints includes:
   (a) an operator display;
   (b) means for displaying the electron backscatter diffraction pattern image on the operator display; and
   (c) an operator input device for defining the plurality of segment endpoints following the curved band in the electron backscatter diffraction pattern image displayed on the operator display.

26. The system of claim 24 wherein the means for calculating the mathematical curve includes means for calculating four cubic spline coefficients for each segment endpoint.

27. The system of claim 18 further comprising memory for saving the correction parameters and means for shifting picture elements in a plurality of electron backscatter diffraction pattern images by amounts determined by the saved correction parameters.

28. The system of claim 18 further comprising means for fill an unfilled portion of the corrected electron backscatter diffraction pattern image with picture elements having a selected intensity.

29. The system of claim 28 wherein the means for filling the unfilled portion of the corrected EBSD pattern image includes means for filling the unfilled portion of the corrected EBSD pattern image with picture elements having an intensity approximately equal to an average intensity of the picture elements in the EBSD pattern image.

30. The system of claim 18 further comprising an operator display for displaying the corrected EBSD pattern image.

31. The system of claim 18 further comprising memory for saving the corrected EBSD pattern image.

* * * * *

UNITED STATES PATENT AND TRADEMARK OFFICE
CERTIFICATE OF CORRECTION

PATENT NO. : 6,555,817 B1
DATED : April 29, 2003
INVENTOR(S) : David Rohde and Patrick P. Camus It is certified that error appears in the above-identified patent and that said Letters Patent is hereby corrected as shown below:

<u>Title page,</u>
Item [57], ABSTRACT,
Line 2, please delete the words "background diffration" and replace them with -- backscatter diffraction --.

<u>Column 12,</u>
Line 2, please delete the word "fill" and replace it with -- filling --.

Signed and Sealed this

Twenty-third Day of September, 2003

JAMES E. ROGAN
*Director of the United States Patent and Trademark Office*